United States Patent [19]

Smeltzer, III et al.

[11] Patent Number: 5,649,934

[45] Date of Patent: Jul. 22, 1997

[54] APPARATUS FOR ASSISTING CHILDBIRTH

[75] Inventors: Stanley S. Smeltzer, III; Seth W. Lawson, both of Huntsville, Ala.

[73] Assignee: The United States of America as represented by the Administrator of the National Aeronautics and Space Administration, Washington, D.C.

[21] Appl. No.: 351,862

[22] Filed: Dec. 6, 1994

[51] Int. Cl.[6] .............................. A61B 17/42; A61B 17/46
[52] U.S. Cl. ....................... 606/122; 606/205; 73/862.541
[58] Field of Search ........................... 606/122, 124, 606/129, 205, 208, 209, 170, 210; 73/862.541, 862.621, 862.629; 128/774, 775, 782

[56] References Cited

U.S. PATENT DOCUMENTS

| | | | |
|---|---|---|---|
| 451,930 | 5/1891 | Hamilton | 606/122 |
| 3,665,925 | 5/1972 | Dersookian | 606/124 |
| 3,785,381 | 1/1974 | Lower et al. | 73/862.541 |
| 4,132,224 | 1/1979 | Randolph | 128/774 |
| 4,204,544 | 5/1980 | Feldstein | 128/774 |
| 4,432,376 | 2/1984 | Huszar | 128/774 |
| 4,487,206 | 12/1984 | Aagard . | |
| 4,842,403 | 6/1989 | Tarbox et al. . | |
| 4,995,401 | 2/1991 | Bunegin et al. | 128/782 |
| 5,431,171 | 7/1995 | Harrison et al. . | |
| 5,493,390 | 2/1996 | Varasi et al. . | |

FOREIGN PATENT DOCUMENTS

| | | | |
|---|---|---|---|
| 382243 | 10/1932 | United Kingdom | 128/323 |

*Primary Examiner*—Robert A. Hafer
*Assistant Examiner*—Justine Yu
*Attorney, Agent, or Firm*—Jerry L. Seemann

[57] ABSTRACT

The invention consists of novel, scissors-like forceps in combination with optical monitoring hardware for measuring the extraction forces on a fetal head. The novel features of the forceps together with knowledge of real time forces on the fetal head enable a user to make a much safer delivery for mother and baby.

12 Claims, 2 Drawing Sheets

APPARATUS FOR ASSISTING CHILDBIRTH

ORIGIN OF THE INVENTION

The invention described in this patent was made by employees of the United States Government and may be manufactured and used by or for the Government for governmental purposes without the payment of any royalties.

BACKGROUND OF THE INVENTION

1. Field of the Invention

This invention pertains to devices for assisting in childbirth. Specifically, the present invention pertains to an improved version of obstetrical forceps.

2. Background Information

Many devices have been developed over the years to assist in the delivery of babies. These devices have included forceps, cylindrical net-like devices, suction devices, and miscellaneous other devices. The forceps typically grasp the fetal head in a scissors-like manner. Examples of such forceps include U.S. Pat. Nos. 3,665,925, 3,785,381, 3,789,849. The cylindrical net-like devices typically grasp the fetal head automatically when tension is applied to the net. Examples of net-like devices include U.S. Pat. Nos. 4,597,391, 4,875,482, 5,122,148, and 5,217,467. The suction devices simply grasp the fetal head with suction. An example of a suction device can be found in U.S. Pat. No. 3,794,044. Other devices include U.S. Pat. No. 3,848,606 (which consists of a concave surface that is attached to the fetal head with an adhesive) and U.S. Pat. No. 5,139,503 (which consists of a pair of spatulas that are attached to and pivot from the ends of a semicircular segment). The goal of all these devices has been to minimize, if not completely eliminate, the risk of injury to both the mother and the fetus. However, as a practical matter, such devices have been ineffective or just too difficult to use.

SUMMARY OF THE INVENTION

This invention has the ability to assist in the safe delivery of a fetus. The invention consists of novel, scissors-like forceps in combination with optical monitoring hardware for measuring the extraction forces on a fetal head. The novel features of the forceps together with knowledge of real time forces on the fetal head enable a user to make a much safer delivery for mother and baby.

An object of this invention is to enable the user to safely grasp and pull on the head of a fetus while assisting in the birthing process.

Another object of this invention is to provide the user with real time knowledge of both the compressive and tractive forces exerted on the head of the fetus.

Still another object of this invention is to automatically limit the maximum compressive force that can be added to the fetal head during delivery.

A further object of this invention is to provide an instrument that can be either easily sterilized for reuse or disposed of at a reasonable cost.

BRIEF DESCRIPTION OF THE DRAWINGS

The following discussion of the invention will refer to the accompanying drawing figures in which:

FIG. 4 is shown partly in section to show the location of the optical means for sensing strain.

DESCRIPTION OF THE PREFERRED EMBODIMENT

A preferred embodiment of this invention comprises scissors-like forceps having flexible spatula ends, a first and a second optical means for sensing strain embedded within the forceps, a means for transmitting an optical signal, a means for receiving a reflected optical signal, an optical fiber connecting the two strain sensing means to the transmitting means and the receiving means, and a means for analyzing and displaying the reflected optical signals.

Figure 1:
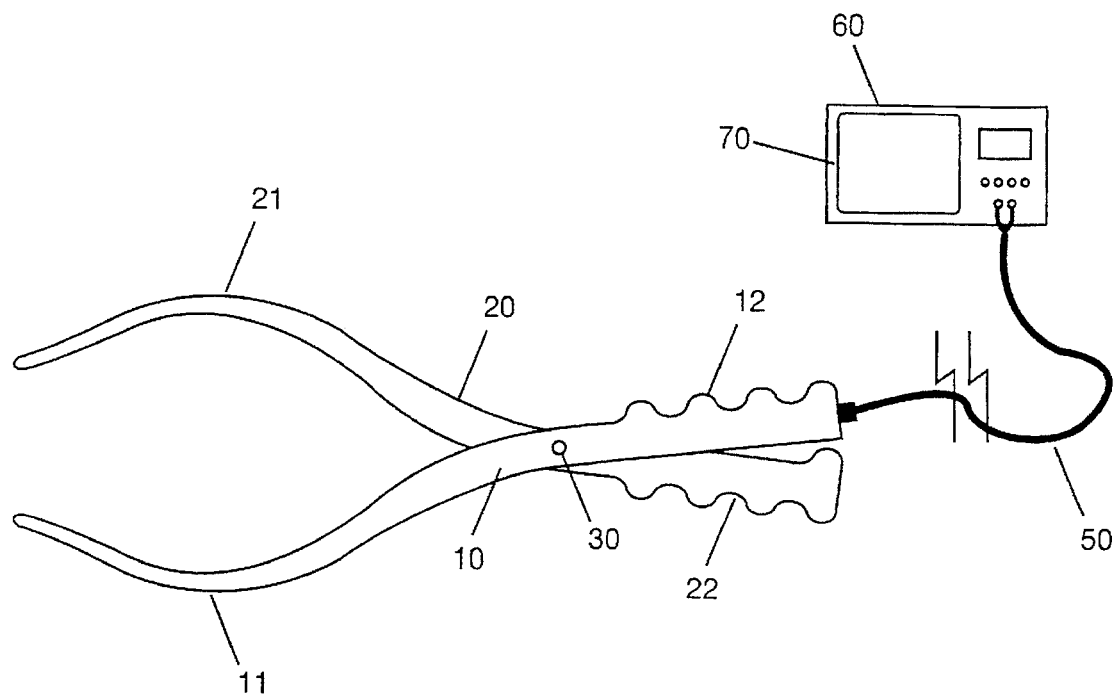
FIG. 1 represents an elevation view of the apparatus for assisting childbirth.

FIG. 1 shows scissors-like forceps consisting of a first member 10 having a flexible spatula end 11 and a rigid handle end 12. Similarly, FIG. 1 shows a second member 20, much like the first member 10, having a flexible spatula end 21 and a rigid handle end 22. A means for pivoting 30 is provided between the flexible spatula ends 11, 21 and the rigid handle ends 12, 22 (located approximately at midpoints of the first and second members) for pivoting the first member 10 relative to the second member 20 in a scissors-like manner. A first and a second optical means for sensing strain 41, 42 (shown in FIG. 4, but not FIG. 1) are embedded within the first member 10 and are connected with optical fiber 50 to a means for transmitting an optical signal 60, which is shown together in FIG. 1 with a means for receiving a reflected optical signal. A means for analyzing and displaying reflected optical signals 70 is shown integrally with the transmitting/receiving means 60 in FIG. 1.

Figure 2:
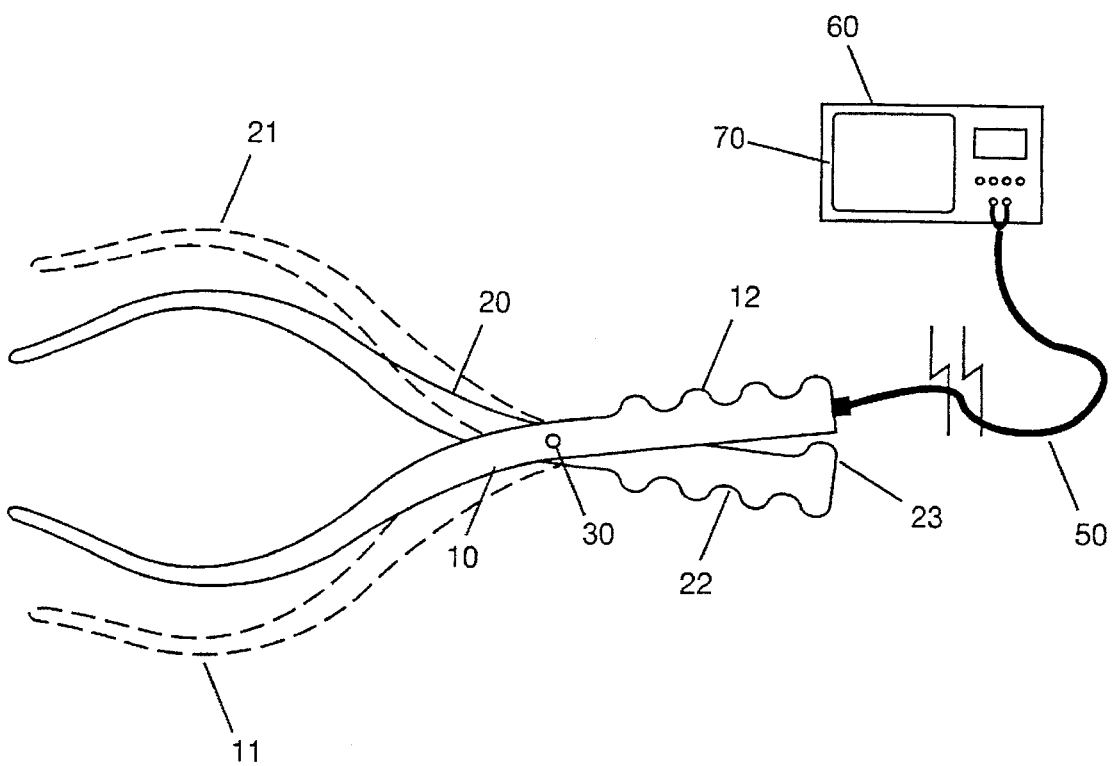
FIG. 2, while being similar to FIG. 1, represents the flexibility of the apparatus with broken lines.

FIG. 2 shows the rigid handle ends 12, 22 in the same position as FIG. 1. However, in FIG. 2, broken lines are used to demonstrate the flexibility of the spatula ends 11, 21 when the forceps are used to grasp the fetal head. A primary advantage of the flexible spatula ends 11, 21 is to prevent injury to the fetal head. Another safety feature is a projection 23 on rigid handle end 22. The projection 23 on rigid handle end 22 prevents the flexible spatula ends 11, 21 from being squeezed further together once the projection 23 comes into contact with the other rigid handle end 12. Thus, the projection 23 automatically limits the maximum compressive force that can be added to the fetal head from the forceps during delivery. Obviously, there are many ways the projection 23 can be fabricated into either the first and/or second member in order to function as an automatic stop.

Figure 3:
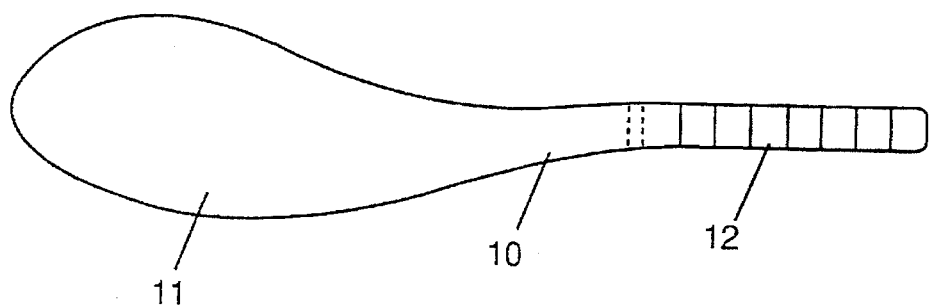
FIGS. 3 and 4 represent orthogonal views of a single member comprising part of the scissors-like forceps belonging to the apparatus.
Figure 4:
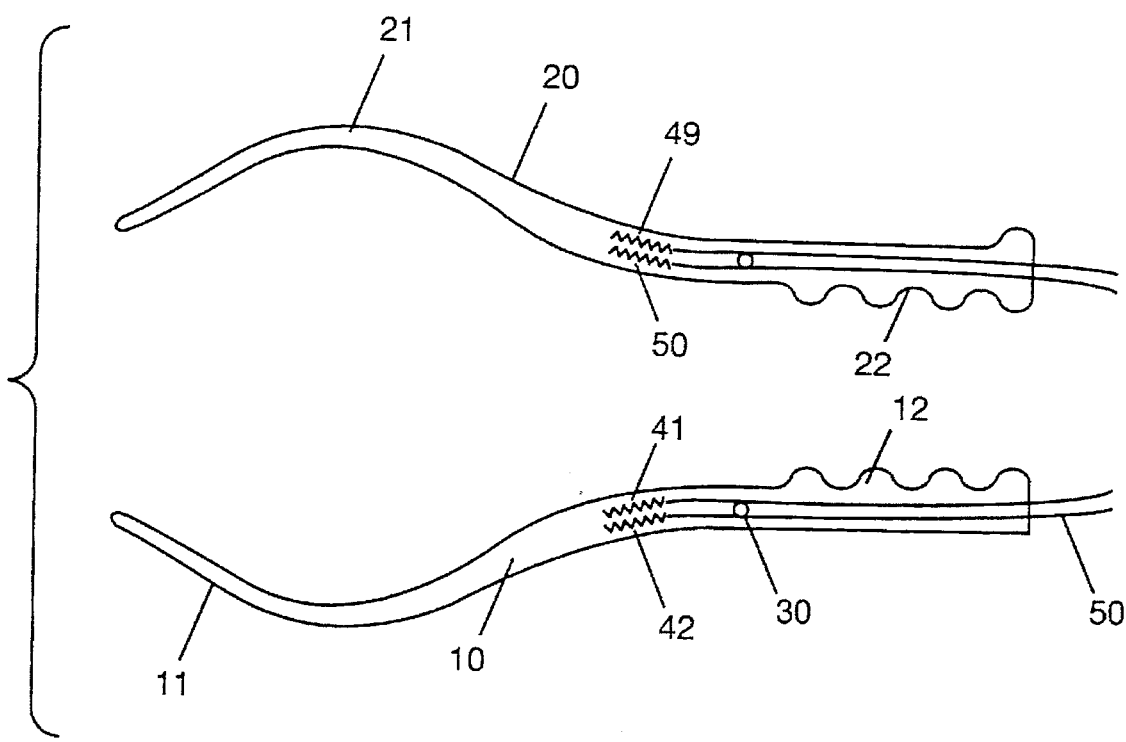

FIGS. 3 and 4 represent orthogonal views of the first member 10. In FIG. 3, the flexible spatula end 11 of the first member 10 is clearly shown. In FIG. 4, the rigid handle end 12 and part of the flexible spatula end 11 are shown in section to demonstrate the placement of the first and second optical means for sensing strain 41, 42. Since a combination of both flexural or bending (from squeezing the fetal head) and tensional (from pulling on the fetal head) forces will be exerted on the first member 10 during the use of this invention, a minimum of two strain sensing means will be required in order to mathematically separate the flexural force from the tensional force. Preferably, the two strain sensing means should be located near extreme bending fibers with one strain sensing means in the compressive bending zone and the other strain sensing means in the tensional bending zone. The preferred bending zone is in the flexible spatula end 11 of the first member 10 adjacent to the means for pivoting 30. The preferred configuration for the strain sensing means is shown in FIG. 4 by the first optical strain sensing means 41 and the second optical strain sensing means 42.

While a number of optical strain sensing means are commercially available, the preferred strain sensing means consists of an optical grating. The optical grating reflects a portion of a transmitted optical signal having a specific wavelength. The wavelength of the reflected signal is proportional to the spacing of the grating. When the spacing of the grating is changed, the wavelength of the reflected optical signal changes. Consequently, by embedding the optical grating within the first member 10, a force-induced strain in the grating will result in a specific change in the wavelength of the reflected signal. In other words, a change in the grating spacing will cause a different portion of the optical signal to be reflected. In addition, by monitoring the change in the wavelength of the reflected signal, the loads induced by the fetal head on the flexible spatula ends 11, 21 of the first and second members 10, 20 (and, inversely, the loads placed on the fetal head by the flexible spatula ends 11, 21 of the first and second members 10, 20) can be determined.

The transmitting/receiving means 60 can be any commercially available system that is capable of transmitting an optical signal and receiving a reflected optical signal. The means for analyzing and displaying reflected optical signals 70 can also be readily accomplished by one having ordinary skill in structural analysis techniques using commercially available equipment. Mathematically separating flexural loads from tensional loads is a very basic structural calculation.

The preferred material for the first and second members 10, 20 is any commercially available thermoplastic material that has been approved for medical applications and that is stable enough to allow sterilization by heat or radiation. The optical grating for the optical means for sensing strain 41, 42 can be fabricated directly into commercially available optical fiber with known methods.

An alternative embodiment of the apparatus for assisting childbirth would be identical to the preferred embodiment described above with one addition. The addition would consists of a pair of strain sensing means for the second member. The addition of a second pair of strain sensing means 49 and 50 to the second member could perform two functions. First, the second pair 49 and 50 could serve as a check or backup for the first pair. Second, the second pair could be used in conjunction with the first pair to monitor more dynamic loading conditions. For example, in the event the forceps needed to be used in a side.-to-side manner rather than in a typical squeeze-and-pull manner, the readings from just one of the members may not give the user a total picture of the forces being exerted on the fetal head. However, if both members were monitored, all possible loads could be identified. A second pair of strain sensing means for the second member can be visualized by referring to FIG. 4.

Before the apparatus for assisting childbirth can be used, the apparatus will first have to be calibrated to account for any differences in operation between the two optical sensors and any differences in placement of the two sensors with respect to the extreme fibers in bending. The best way to calibrate the apparatus is to compare the reflected signal from both sensors under a zero-load condition to the reflected signal from both sensors while the first and second members are being subjected to a pure, predetermined flexural load. A pure flexural load can be obtained by squeezing an object with the spatula ends of the first and second members. By knowing how the sensors respond to a pure flexural load, any combination load can be mathematically separated into its flexural and tensional components.

Once the apparatus has been calibrated, it can be used like any ordinary set of obstetrical forceps. However, with this apparatus, the user will know exactly how much pressure and traction is being exerted on the fetal head.

What is claimed is:

1. An apparatus for assisting in the delivery of a fetus, comprising a first member, said first member having a flexible spatula end which terminates in a free end and a handle end;

a second member, said second member having a flexible spatula end which terminates in a free end and a handle end;

means for pivoting said first member relative to said second member, said pivoting means being positioned on said first and second members between said spatula and handle ends, first optical means embedded within one of said members in at a location spaced from said free end and in the member location to sense strain caused by bending forces, and second optical means embedded within said one of the members at a location spaced from said free end and in a position to sense strain caused by tensile forces applied to said one member.

2. An apparatus for assisting in the delivery of a fetus as recited in claim 1, further comprising:

means for transmitting an optical signal;

means for receiving a reflected optical signal;

an optical fiber connecting said first and second optical means for sensing strain to said means for transmitting an optical signal and said means for receiving a reflected optical signal; and means for analyzing and displaying reflected optical signals connected to said receiving means.

3. An apparatus for assisting in the delivery of a fetus as recited in claim 2 wherein said first and second members are fabricated from thermoplastic material.

4. An apparatus for assisting in the delivery of a fetus as recited in claim 2, further comprising:

third optical means for sensing strain embedded within said second member;

fourth optical means for sensing strain embedded within said second member; and another optical fiber connecting said third and fourth optical means for sensing strain to said means for transmitting an optical signal and said means for receiving a reflected optical signal.

5. An apparatus for assisting in the delivery of a fetus as recited in claim 1, further comprising: a projection on said handle end of said first member.

6. An apparatus for assisting in the delivery of a fetus as recited in claim 1 wherein said first and second optical means for sensing strain are embedded in said flexible spatula end of said first member adjacent to said pivoting means.

7. An apparatus for assisting in the delivery of a fetus as recited in claim 6 wherein said first and second optical means for sensing strain are an optical gratings.

8. An apparatus for assisting in the delivery of a fetus, comprising a first member, said first member having a flexible spatula end, a midpoint, and a handle end;

a second member, said second member having a flexible spatula end, a midpoint, and a handle end, said members being pivotally connected to each other at a pivot point adjacent to said midpoint;

first optical means for sensing bending strain embedded within said first member at a location adjacent to said midpoint in a position to sense bending strain;

second optical means for sensing strain embedded within said first member at a location adjacent to said midpoint in a position to sense tensile strain;

means for transmitting an optical signal;

means for receiving a reflected optical signal;

an optical fiber connecting said first and second optical means for sensing strain to said means for transmitting an optical signal and said means for receiving a reflected optical signal; and means for analyzing and displaying reflected optical signals connected to the means for receiving a reflected signal.

9. An apparatus for assisting in the delivery of a fetus as recited in claim 8, further comprising: a projection on said handle end of said first member.

10. An apparatus for assisting in the delivery of a fetus as recited in claim 8 wherein said first and second members are fabricated from thermoplastic material.

11. An apparatus for assisting in the delivery of a fetus as recited in claim 8, further comprising:

third optical means for sensing strain embedded within said second member;

fourth optical means for sensing strain embedded within said second member; and another optical fiber connecting said third and fourth optical means for sensing strain to said means for transmitting an optical signal and said means for receiving a reflected optical signal.

12. An apparatus for assisting in the delivery of a fetus as recited in claim 8 wherein said first and second optical means for sensing strain are optical gratings.

* * * * *